US005351682A

United States Patent [19]

Foote

[11] Patent Number: 5,351,682

[45] Date of Patent: Oct. 4, 1994

[54] BREATHING DEMAND REGULATIONS

[75] Inventor: James C. Foote, Yeovil, England

[73] Assignee: Normalair-Garrett (Holdings) Ltd., Yeovil, England

[21] Appl. No.: 43,526

[22] Filed: Apr. 6, 1993

[30] Foreign Application Priority Data

Apr. 16, 1992 [GB] United Kingdom ................. 9208481

[51] Int. Cl.5 ............................................ A61M 15/00

[52] U.S. Cl. .......................... 128/205.24; 128/204.26; 137/494; 137/81.1

[58] Field of Search .............................. 137/494, 81.1; 128/201.29, 202.11, 202.19, 202.12, 204.26, 204.29, 204.18, 205.26, 205.24, 204.23, 201.28, 204.26; 600/19, 20

[56] References Cited

U.S. PATENT DOCUMENTS

| | | | |
|---|---|---|---|
| 4,651,728 | 3/1987 | Gupta et al. | 128/201.28 |
| 4,856,507 | 8/1989 | Ouillon et al. | 128/204.26 |
| 4,858,606 | 8/1989 | Hamlin | 128/204.29 |
| 4,919,124 | 4/1990 | Stevenson et al. | 128/202.26 |
| 5,199,426 | 4/1993 | Aldworth et al. | 128/205.24 |
| 5,247,926 | 9/1993 | Harral | 128/202.11 |

FOREIGN PATENT DOCUMENTS

| | | | |
|---|---|---|---|
| 661702 | 4/1963 | Canada | 128/204.29 |
| 1784227 | 5/1973 | Fed. Rep. of Germany | 128/205.24 |
| 1456074 | 10/1966 | France | 128/204.29 |

*Primary Examiner*—Edgar S. Burr
*Assistant Examiner*—Eric P. Raciti
*Attorney, Agent, or Firm*—Larson & Taylor

[57] ABSTRACT

An aircrew breathing regulator having facility for mixing ambient air with oxygen-enriched breathing gas in supplying breathing gas to an end user, includes a demand valve connected between an inlet for receiving oxygen-enriched breathing gas and an outlet for delivering breathing gas to the end user. Ambient air is entrained by flow of oxygen-enriched breathing gas through an injector nozzle to enter an ambient air inlet and mix with the oxygen-enriched breathing gas downstream of the demand valve. Pressure build-up downstream of the demand valve resulting from the flow restricting effect of the injector nozzle causes a pressure feedback onto a head of the valve tending to force it closed. This is overcome by nullifying the action on the demand valve of downstream pressure so that the valve is pressure balanced.

7 Claims, 3 Drawing Sheets

BREATHING DEMAND REGULATIONS

BACKGROUND OF THE INVENTION

1. Field of the Invention

This invention relates to breathing demand regulators and is particularly concerned with breathing demand regulators having facility for mixing air with oxygen enriched breathing gas in aircraft breathing systems.

2. Description of the Prior Art

It is known practice to supply 100% oxygen gas for aircraft aircrew breathing purposes from a liquid oxygen (LOX) system which converts liquid oxygen to gaseous oxygen in a converter. The gaseous oxygen is delivered to an aircrew breathing mask byway of a regulator having a valve member that opens to allow oxygen to flow to the mask in response to the breathing demands of the aircrew member.

At lower altitudes, generally below 9000 m (30000 ft), the aircrew member may become over oxygenated if 100% oxygen gas is supplied for breathing purposes. It is usual, therefore, for the regulator to include a facility for entrainment of ambient air to reduce the content of oxygen in the breathing gas delivered to the breathing mask. Disclosures of such breathing regulators are to be found, for example, in U.S. Pat. No. 2,384,669; GB-A-630,740; and U.S. Pat. No. 4,928,682.

Whilst aircraft having LOX systems continue in operation at the present time, it is generally the practice in new aircraft designs to provide an on-board oxygen generating system (OBOGS) in which oxygen-enriched breathable gas is derived from a molecular sieve oxygen concentrator (MSOC). The MSOC comprises two or more molecular sieve beds which retain nitrogen in air supplied to the beds so that product gas enriched in oxygen is delivered from the MSOC. Each sieve bed is cycled between an on-stream phase in which air is supplied to the bed and oxygen-enriched product gas is delivered from the bed, and an off-stream phase in which the bed is vented to ambient and back-flushed with oxygen-enriched product gas to cleanse it of retained nitrogen ready for the next on-stream phase. Cycling of the beds may be controlled to produce product gas of maximum oxygen concentration, usually between 90% and 95% oxygen, or the beds may be cycled to produce product gas enriched with oxygen to a concentration appropriate to maintaining oxygen partial pressure in the product gas at a constant value substantially equivalent to sea level partial pressure of oxygen in air, irrespective of the altitude of the aircraft. Whilst in some aircraft aircrew breathing systems employing an OBOGS for supplying breathable gas the latter method of control is used, in other systems preference is for the former method of control. In either case product gas is delivered to an aircrew member by way of a breathing demand regulator which in the case where the product gas is of maximum oxygen concentration has provision for entrainment of air to reduce the oxygen concentration at lower altitudes.

There is now a need for a breathing regulator capable of operating with both LOX and OBOGS systems. This imposes a requirement for a breathing regulator capable of operating over a wide range of inlet pressure and, in particular, down to very low inlet pressures, for example, 70 kPa (10 psi), under certain aircraft operating conditions.

Breathing demand regulators, by virture of having to present minimum resistance to breathing efforts of an aircrew member, should critically balanced mechanisms and as such are sensitive to variations in pressure loading of a main demand valve which results from variations in both upstream and downstream conditions.

In its simplest form, in a breathing demand regulator using 100% OBOGS product gas, the mechanism consists of a sensing member, usually a diaphragm, which is linked either mechanically or pneumatically to the demand valve. The loading of this mechanism from a combination of pneumatic and spring forces, ensures that under zero demand conditions the demand valve remains closed but with minimum reduction in pressure on one side of the sensing diaphragm resulting from inhalation by the aircrew member, the demand valve is opened and flow is delivered to satisfy demand.

All breathing demand regulators are subject to variation in upstream conditions (supply pressure variations) but where possible these are minimised by utilising a pressure reducing valve or pressure limiting valve either upstream of the regulator or integral with the regulator. However, some systems do not afford this facility and the demand mechanism has to cope with wide variations in supply pressure, typically in regulators which are required to operate with an OBOGS and, in some cases, also to be compatible with LOX systems.

A breathing demand regulator disclosed in EP-A-0,078,644 (Normalair-Garrett) overcomes both the problem of large variations in supply conditions and the problem of demand valve operation at the lower range of oxygen-enriched breathable gas pressure available from a MSOC, particularly at the lower end towards 70 kPa (10 psi). This regulator embodies a diaphragm arranged for sensing breathing demand and actuating, via a lever, a demand valve having a Valve head carried by a stem projected by a spool member. Opposed surface areas of the valve head and spool member are equal so that the valve is balanced by the pressure of oxygen-enriched breathing gas entering an inlet disposed therebetween and variations in upstream pressure are of no effect.

U.S. Pat. No. 4,928,682 (Normalair-Garrett) discloses a modified form of the aforementioned breathing demand regulator (EP-A-0,078,644) having facility for entrainment of ambient air for mixing with maximum concentration oxygen-enriched product gas supplied to the regulator whereby breathing gas of reduced oxygen enrichment may be supplied to an aircrew member. The inventive feature of this disclosure relates to control of an injector nozzle bypass whereby in one mode of regulator operation an ambient air inlet control valve is closed and an injector bypass is open so that undiluted MSOC product gas is delivered to a regulator outlet, and in another mode of operation the air inlet control valve is open and the injector bypass is closed so that MSOC product gas flows through the injector nozzle to induce ambient air to enter the regulator and mix with the MSOC product gas whereby breathable gas of diluted oxygen concentration is delivered to the regulator outlet.

For efficiency of operation in the airmix mode the modified regulator depends upon driving pressure behind the injector nozzle to create the necessary pressure drop across the nozzle and hence the energy to entrain air through the air inlet control valve. The driving pressure is a function of flow and nozzle size. The flow varies from zero to a maximum, depending upon the size of the demand made on the regulator, therefore the efficiency varies from zero to some value related to the nozzle size.

The nozzle size invariably has to be a compromise:

i. it has to be of a size which will provide the required efficiency in terms of air/oxygen mixture over the full range of breathing flows;

ii. it has to be sufficiently large to pass the minimum amount of MSOC oxygen enriched product gas at peak flow demands;

iii. in order to meet i. it has to remain seated for most of the demand flow range but may have to relieve at the top end of the flow range to meet ii;

iv. it has to be as large as possible to reduce the tendency towards oscillatory activity;

v. it has to be as large as possible to reduce the downstream feedback onto the demand valve which has a detrimental effect on breathing.

There is a direct conflict between the requirements to meet i. and those to meet ii. to v. inclusive. Furthermore, if the regulator incorporates a flow indicator which relies for its operation on injector driving pressure, this imposes yet another function on the injector system since the nozzle then has to be small enough to generate a high enough pressure to operate the flow indicator mechanism within the required limits.

Development of an airmix regulator based on the disclosure of U.S. Pat. No. 4,928,682 has highlighted all the difficulties previously experienced with the development of airmix regulators and, unfortunately, the point made at v., above has shown itself to be more of a problem than was originally expected, particularly in a system where a high boost characteristic is required to overcome high system back pressure. Pressure build-up downstream of the demand valve resulting from the flow restricting effect of the injector nozzle causes a pressure feedback onto the head of the valve tending to force it closed. To overcome this effect the aircrew member must suck harder when demanding breathing gas so that breathing effort becomes more tiresome, or additional boost must be built into the regulator by changing the configuration of the demand sensing region in the outlet of the regulator which makes it more difficult to control overshoot of the demand valve on opening.

SUMMARY OF THE INVENTION

It is an object of the present invention to provide an aircrew breathing demand regulator having facility for mixing ambient air with oxygen-enriched breathing gas supplied to the regulator which overcomes the aforementioned problems.

In meeting this object the present invention provides an aircrew breathing demand regulator for controlling delivery of breathing gas in accordance with breathing demands of an end user, comprising a regulator body having an inlet for receiving a flow of oxygen-enriched breathing gas and an outlet for delivering breathing gas to the end user, a demand valve connected between the inlet and the outlet for controlling flow of oxygen-enriched breathing gas from the inlet to the outlet, breathing demand sensing means connected with the demand valve and operable in response to sensed breathing demand at the outlet for moving the demand valve towards opening whereby oxygen-enriched breathing gas flows from the inlet to the outlet, ambient air inlet means including ambient air control valve means and ambient air entrainment means for entraining ambient air to enter the ambient air inlet means and mix with oxygen-enriched breathing gas downstream of the demand valve whereby breathing gas of diluted oxygen concentration is delivered at the outlet, and demand valve pressure balancing means for nullifying the action on the demand valve of pressure downstream of the demand valve.

The oxygen-enriched breathing gas inlet is adapted for connection to a source of oxygen-enriched breathing gas which may be 100% oxygen gas delivered by a liquid oxygen system or oxygen-enriched breathing gas delivered by a molecular sieve oxygen concentrator (MSOC). In the latter case the breathing gas delivered by the MSOC will be enriched with oxygen to a percentage concentration (usually 90% or greater) such that it can be mixed with ambient air to provide breathing gas of appropriately reduced oxygen concentration for breathing at altitudes below 9000 m (30000 ft).

The regulator outlet is adapted for connection to a face mask worn by an aircrew member breathing from a system embodying the regulator.

Demand valve pressure balancing means for nullifying the action on the demand valve of pressure downstream of the demand valve may comprise means for applying downstream pressure as a balancing force acting on the demand valve in a direction opposing the action of downstream pressure tending to force the demand valve closed.

The means for applying pressure downstream of the demand valve as a balancing force preferably comprises a balancing member of equal area to a valve head of the demand valve and means for allowing downstream pressure to act on the balancing member whereby a force is applied to the demand valve to oppose the action of downstream pressure tending to force the valve closed.

In one embodiment of the invention the balancing member comprises a piston acting on an end of the demand valve opposite to an end which projects a valve head, the piston having a face of equal area to an end face of the valve head exposed to downstream pressure.

In another embodiment of the invention the balancing member comprises a stem projected by a downstream end face of a valve head of the demand valve, and a diaphragm connecting between the stem and a downstream passage wall of the regulator body for supporting the stem, a face of the diaphragm opposed to the downstream end face of the valve head having an effective area equal to the opposed end face area of the demand valve head.

Alternatively, the demand valve pressure balancing means may comprise means for nullifying pressure downstream of the demand valve may comprise means for inhibiting feedback of downstream pressure onto a head of the demand valve which would tend to force the demand valve towards closing.

In an embodiment of the invention means for inhibiting feedback of downstream pressure onto the demand valve head comprises forming the demand valve head as a piston sliding in a bore which is vented to a demand pressure sensing chamber of the regulator. Alternatively, the bore may be vented to aircraft cabin pressure.

The demand valve may comprise a valve head supported by a spindle from a spool which slides in a bore in the regulator body, opposed faces of the valve head and the spool being exposed to pressure of oxygen-enriched breathing gas entering the regulator inlet (upstream pressure) and being of equal area so that the demand valve is balanced with respect to upstream pressure.

Breathing demand sensing means for moving the demand valve towards opening may comprise a demand pressure sensing chamber having connection with the regulator outlet and being separated from a demand pressure control chamber by a diaphragm arranged to bear on a pivoted operating lever located in the demand pressure sensing chamber and being adapted to contact the demand valve for movement thereof.

BRIEF DESCRIPTION OF THE DRAWINGS

The invention will now be further described byway of example only and with reference to the accompanying drawings, in which.

DETAILED DESCRIPTION OF THE DRAWINGS

Figure 1:
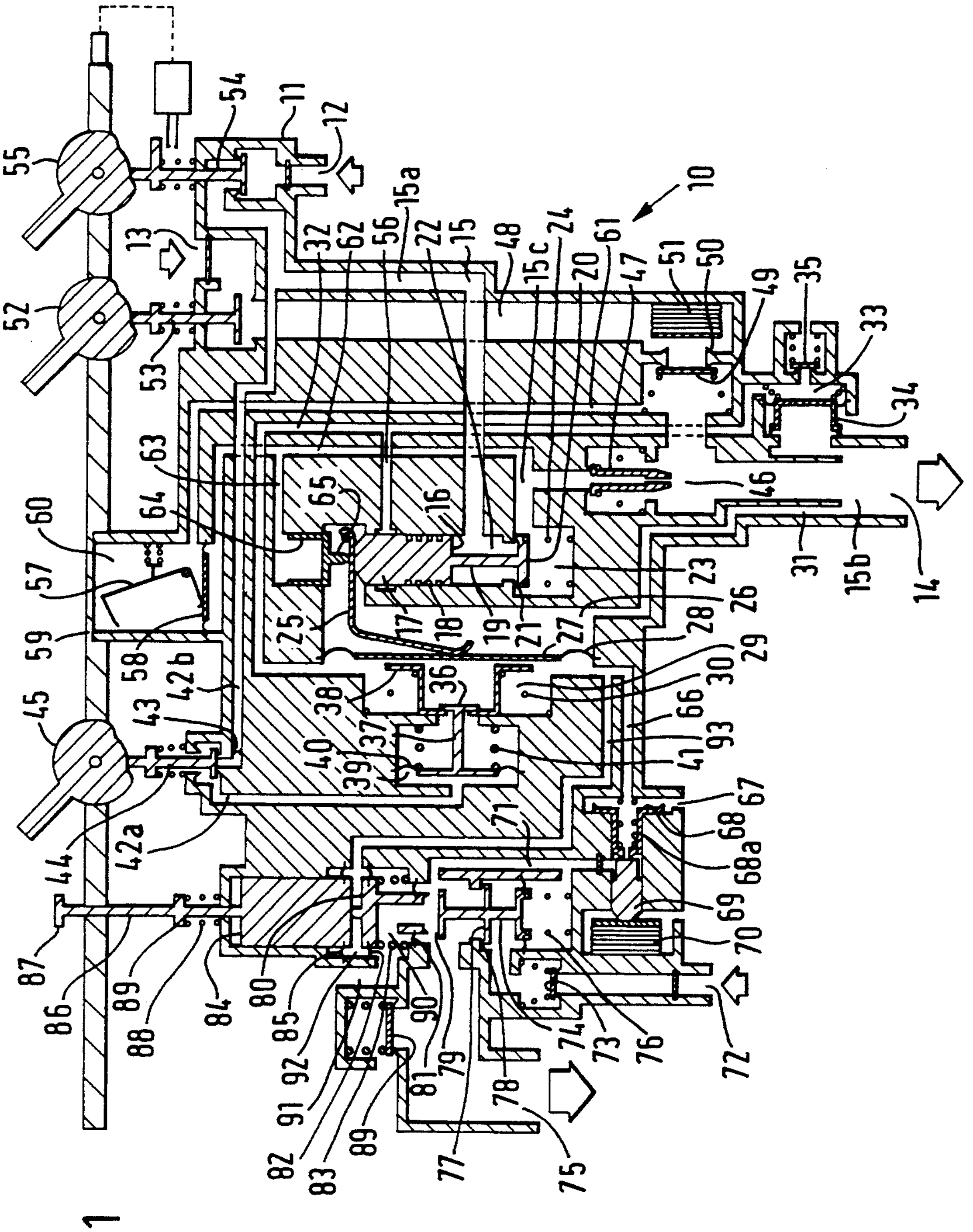
FIG. 1 is a schematic illustration of a breathing demand regulator in accordance with one embodiment of the invention.

Referring now to FIG. 1, an aircraft aircrew breathing demand regulator 10 comprises a regulator body 11 having a breathing gas inlet 12 adapted for connection to a source of oxygen gas or oxygen-enriched breathing gas (not shown), an ambient air inlet 13, and a breathing gas outlet 14 adapted for connection to a face mask (not shown) worn by the aircraft aircrew member. The breathing gas inlet 12 is connected to the breathing gas outlet 14 by a flowpath 15 that includes a demand valve 16. The demand valve 16 comprises a spool piston 17 having labyrinth grooves 18 in its external surface. The piston 17 is joined by a reduced diameter stem 19 to a valve head 20 associated with a valve seat 21 which separates an inlet chamber 22 from an outlet chamber 23. The inlet chamber 22 is connected by an inlet passageway 15*a* of the flowpath 15 with the breathing gas inlet 12. The valve head 20 is biased towards the seat 21 by a spring 24.

The end of piston 17 contacts a pivoted lever 25 which extends into a demand pressure sensing chamber 26 for contact by a plate 27 supported by a sensing diaphragm 28 which separates chamber 26 from a control pressure chamber 29. A spring 30 is located in chamber 29 for biasing the sensing diaphragm 28 to produce a safety pressure in the face mask as will hereinafter be described.

Sensing chamber 26 is pneumatically connected through passage 31 with outlet passageway 15*b* of flowpath 15. Control pressure chamber 29 is pneumatically connected through passageway 32 to a chamber 33 of a spring-loaded compensated dump valve 34. A spring-loaded pressure relief valve 35 is provided for venting chamber 33 to ambient if control pressure exceeds a predetermined maximum.

A flanged end 36 of a safety pressure control member 37 is slideably located through a dished support plate 38. Member 37 projects into a chamber 39 to have its opposite end supported by a diaphragm 40. A spring 41 acts between the regulator body and the diaphragm 40 to bias the pressure control member 37 to a position in which it holds the support plate 38 away from the diaphragm supported plate 27. Chamber 39 is connected by passageways 42*a* and 42*b* for receiving a bleed of breathing gas from inlet passageway 15*a*. Passageway 42*b* incorporates a flow restrictor orifice 43 and may be closed with respect to passageway 42*a* by a valve 44 operated by a switch 45 and shown in a closing position in FIG. 1 whereby chamber 39 and passageway 42*a* are communicated to aircraft cabin.

In obtainment of safety pressure in the face mask, the switch 45 is moved to its opposite position in which valve 44 closes the vent to cabin ambient and communication between passageways 42*a* and 42*b* is made so that a bleed of gas from breathing gas inlet passageway 15*a* flows to chamber 39 to build up a pressure therein sufficient to overcome the biasing action of spring 41 and move flanged end 36 of control member 37 away from support plate 38. The spring 30 is then able to exert itself and apply a biasing action on diaphragm mounted plate 27 which rocks lever 25 about its pivot to slightly open demand valve 16. This allows sufficient breathing gas to flow to the face mask to build up a small positive pressure therein with respect to ambient so that ingress of cabin ambient air is precluded.

An ambient air mixing chamber 46 provided in flowpath 15 downstream of the outlet chamber 23 receives an outlet end of an injector nozzle 47 having its opposite end located for receiving flow from chamber 23 by way of connecting passageway 15*c*. The mixing chamber 46 is pneumatically connected through a passageway 48 with ambient air inlet 13, this connection being closed by a spring-loaded valve plate 49 which seats with one side of a double valve seat 50 when there is no breathing demand at the outlet 14. Communication between mixing chamber 46 and air inlet 13 is also closed above a predetermined aircraft cabin altitude, generally 9000 m (30000 ft), by an aneroid valve 51 which expands to close with the other side of double valve seat 50. Dilution of oxygen-enriched breathing gas is also at the discretion of the aircrew member who may select "Dilution Off" by operation of a switch 52 to a position opposite that shown in FIG. 1 so as to move a valve member 53 to a position in which it closes communication between ambient air inlet 13 and passageway 48.

A valve member 54 is provided for closing communication between breathing gas inlet 12 and flowpath 15, as shown in FIG. 1, and is moved by operation of a switch 55 to a position opposite that shown in FIG. 1 to open this communication.

With communication being made between breathing gas inlet 12 and flowpath 15, and with oxygen-enriched breathing gas available at the inlet 12, variations in breathing gas pressure upstream of demand valve head 20 are of no effect because the areas of the opposed faces of the demand valve head and the spool piston 17 are equal so that the demand valve 16 is balanced with respect to upstream pressure.

Leakage of breathing gas past the labyrinth grooves 18 of spool piston 17 is bled to control pressure chamber 29 by a passageway 56 connecting with passageway 32.

In operation of the regulator, when a breathing demand is sensed in demand pressure sensing chamber 26 the diaphragm 28 is moved to the right as seen in FIG. 1, which rocks the lever 25 about its pivot to move the spool piston 17 downwardly and with it the valve head 20 so that breathing gas flows from inlet chamber 22 to outlet chamber 23 and then by way of injector nozzle 47 to breathing gas outlet 14.

An indication of breathing gas flow is given by a pivoted arm 57 which is moved by a diaphragm supported plate 58 to mask a window 59 forming one wall of a chamber 60 in which the arm 57 is located. The chamber 60 is communicated by passageway 61 with pressure downstream of injector nozzle 47 whilst the opposite face of the diaphragm supported plate 58 is communicated by a passageway 62 with pressure in outlet chamber 23. Thus in the presence of breathing gas flow the pressure differential across the injector nozzle is effective to move the diaphragm supported plate to cause the pivoted arm 57 to mask the window 59.

Pressure build-up in the outlet chamber 23 downstream of the demand valve head 20 resulting from the flow restricting effect of the injector nozzle 47 causes a pressure feedback on the demand valve head which acts with spring 24 to tend to close the demand valve. Thus the aircrew member has to suck harder to maintain the demand valve open so as to obtain a flow of oxygen-enriched breathing gas. In this embodiment of the present invention this problem is overcome by balancing the demand valve 16 with respect to downstream pressure. Pressure in outlet chamber 23 is communicated by a branch passageway 63 with one face of a cup-shaped piston 64 that projects a stem 65 from its opposite face into contact with pivoted lever 25 and, hence, spool piston 17 of demand valve 16. The face of piston 64 exposed to outlet chamber pressure is of equal area to the downstream end face of demand valve head 20 so that an equal and opposite force is applied to the demand valve to oppose the action of outlet chamber pressure on the downstream end face of demand valve head 20.

Breathing pressure control chamber 29 is pneumatically connected with aircraft cabin pressure byway of passageway 66 and outlet 67. Bleed from chamber 29 to aircraft cabin is controlled by pressure breathing control valve 68 having a stem **68*a* slideable in a bore in the regulator body. An end face of the stem 68*a* is arranged for being actuated by a loading member 69 in contact with an aneroid capsule 70 which expands if aircraft cabin pressure exceeds a predetermined ambient altitude equivalent, generally 12000 m (40000 ft), to move control valve 68 towards closing communication between passageway 66 and outlet 67. This end face of the valve stem is communicated also with pressure in a G-suit inflation air outlet 75 byway of a passageway 71. This arrangement is similar to that disclosed by EP-A-0448258 (Normalair-Garrett) and, in operation, provides for pressure in breathing pressure control chamber 29 to be increased appropriate to raising the breathing gas pressure at breathing gas outlet 14** for positive pressure breathing whereby a physiologically acceptable level of oxygen partial pressure is maintained in the breathing gas supplied to the aircrew member during flight at cabin altitudes in excess of 12000 m or in the presence of accelerations along the aircraft vertical axis of 2 G or greater. The arrangement also provides for the higher of two pressure schedules for positive pressure breathing with altitude and positive pressure breathing with G to be selected in the event of simultaneous exposure to high altitude and G-load.

In this embodiment G-suit inflation control means is provided integrally with the regulator body 11 for controlling supply of high pressure air to inflate a trouser garment worn by the aircrew member in the presence of high G, generally 2 G or higher. High pressure air from a source (not shown) is made available to a high pressure air inlet 72 and flows by way of a passageway that incorporates a spring loaded check valve 73 and a diaphragm supported main valve member 74 to inflation air outlet 75 which is adapted for connection with the G-suit (not shown). The main valve member 74 is biased by a spring 76 towards closing a valve head 77 with a valve seat 78 whereby communication between air inlet 72 and air outlet 75 is closed. The head 77 projects a stem having a flanged end face 79 towards a valve head end of a vent valve 80 which is supported near to its valve head end by a diaphragm 81 and near to its opposite end by a diaphragm 82. Valve 80 is biased by a spring 83 towards contact at its opposite end with an inertia mass 84 which is supported by a diaphragm 85, the mass 84 being slideable in a bore in the regulator body 11. The inertia mass 84 projects a stem 86 which terminates in a flanged end 87 in provision of a press-to-test feature. The inertia mass 84 is off-loaded from vent valve 80 by a spring 88 which acts between the regulator body 11 and a second flange 89 provided on the stem 86 between the inertia mass 84 and the flanged end 87. Vent valve 80 has a hollow valve stem incorporating an aperture 90 by which the interior of the valve stem is placed in communication with a vent outlet 91 in the regulator body 11. A chamber 92 defined by opposed diaphragms 82 and 85 of vent valve 80 and inertia mass 84, respectively, is communicated by a passageway 93 with breathing pressure control chamber 29.

During flight of an aircraft in which regulator 10 is fitted, below cabin altitudes of 12000 meters and with a load of one G, breathing pressure control chamber 29 is vented to aircraft cabin by way of outlet 67, and valve head 77 of main valve member 74 is closed with valve seat 78 so that the G-suit (not shown) is vented to cabin by way of air outlet 75, aperture 90 in the valve stem of vent valve 80, and outlet 91. As acceleration along the aircraft vertical axis builds to impose a load above one G this is sensed by the inertia mass 84 which overcomes the bias of springs 83 and 88 and exerts a force on vent valve 80 to cause the valve head end to commence to close with flanged end 79 of main valve member 74 thereby restricting the vent path from the G-suit. As the load builds, say towards 2 G, vent valve 80 is closed with flanged end 79 of main valve member 74 which commences to open so that high pressure air from air inlet 72 flows to air outlet 75, to inflate the G-suit. The level of pressure in the G-suit is controlled by the suit pressure sensed at the outlet 75 which acts on diaphragm 81 to balance the downward force of inertia mass 84. Air pressure at outlet 75 which is closely related to G-suit infliction pressure, is sensed in passageway 71 and acts on pressure breathing control valve 68 to move it towards restricting bleed outflow from breathing pressure control chamber 29 whereby pressure in chamber 29 is increased in obtainment of positive pressure breathing for further protection of the aircrew member against the effect of G-load.

If the aircraft experiences a cabin decompression when operating at an altitude in excess of 12000 meters, aneroid capsule 70 expands to move the pressure breathing control valve 68 through loading member 69 towards restricting outflow from the breathing pressure control chamber 29 whereby pressure in chamber 29 is increased in obtainment of positive pressure breathing for protection of the aircrew member against exposure to high altitude (low ambient pressure). This restriction allows pressure to build also in passageway 93 and chamber 92 to overcome the biasing action of spring 83 so that the vent valve 80 is moved into contact with flanged end face 79 of main valve 74 thereby closing vent outlet 91. As pressure in chamber 92 continues to build the biasing action of spring 76 on main valve 74 is overcome and the main valve moves towards opening to allow pressurised air to flow from inlet 72 to outlet 75 to inflate the G-suit for further protection of the aircrew member against exposure to high altitude.

In the event that the aircrew member is subjected to G-load following cabin decompression with the aircraft operating at cabin altitudes in excess of 12000 m, the aneroid capsule 70 and pressure breathing control valve 68 coact to control outflow from control chamber 29 to increase breathing gas delivery pressure at outlet 14 appropriate to protection required at the particular altitude. If however the regulator is simultaneously exposed to both high altitude and high acceleration the higher of the altitude and G-load requirements will be satisfied as is more fully discussed in EP-A-0448258.

A spring loaded maximum pressure relief valve 89 is provided at outlet 75 whereby pressure in the G-suit may vent to aircraft cabin in the event that a predetermined safe inflation pressure is exceeded.

Figure 2:
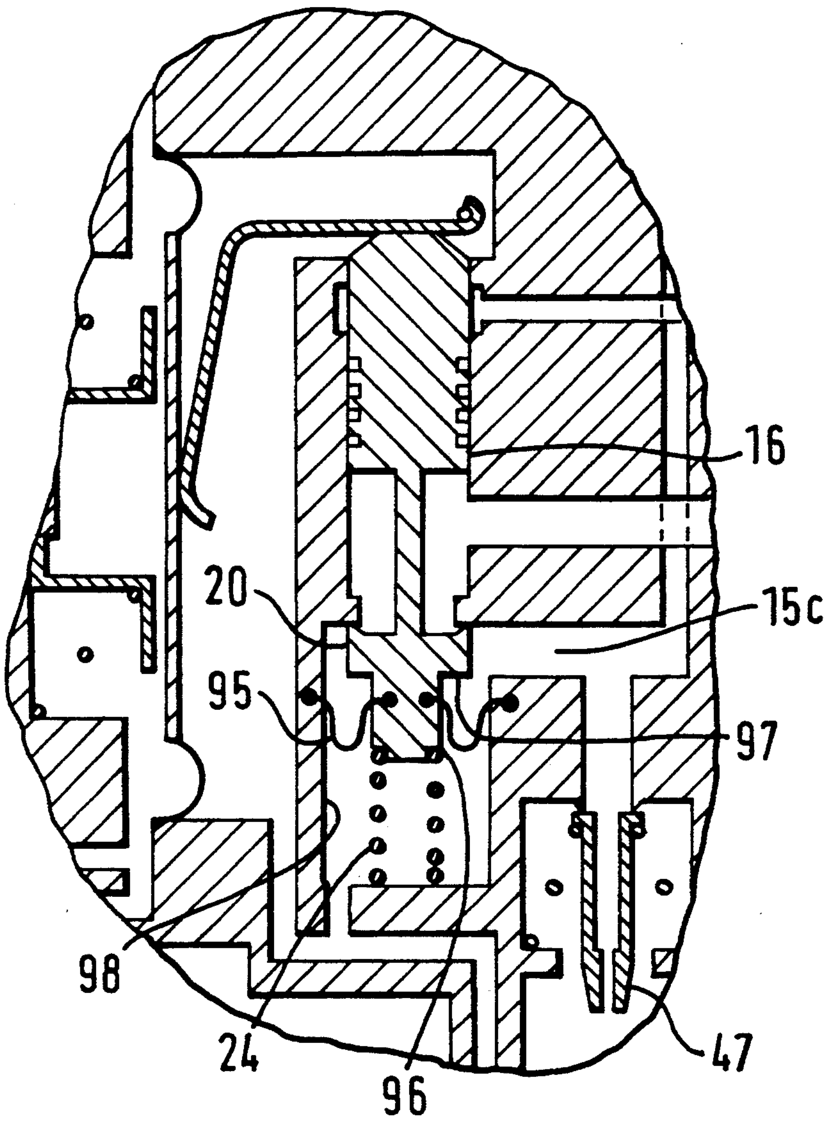
FIG. 2 is a schematic illustration of a part of a breathing demand regulator in accordance with another embodiment of the invention.

An aircrew breathing demand regulator in accordance with another embodiment of the invention, reference FIG. 2, has the demand valve 16 balanced with respect to pressure downstream of the demand valve head 20 by a balancing member comprising a rolling diaphragm 95 attached between a stem 96 projected from an end face 97 of the demand valve head 20 and the wall of a bore 98 in the regulator body 11. The effective area of the rolling diaphragm 95 opposed to the end face 97 of the demand valve head 20 is of equal area to the end face so that the action of pressure downstream of the valve head 20 is balanced. In other respects the regulator is the same as that previously described with reference to FIG. 1.

Figure 3:
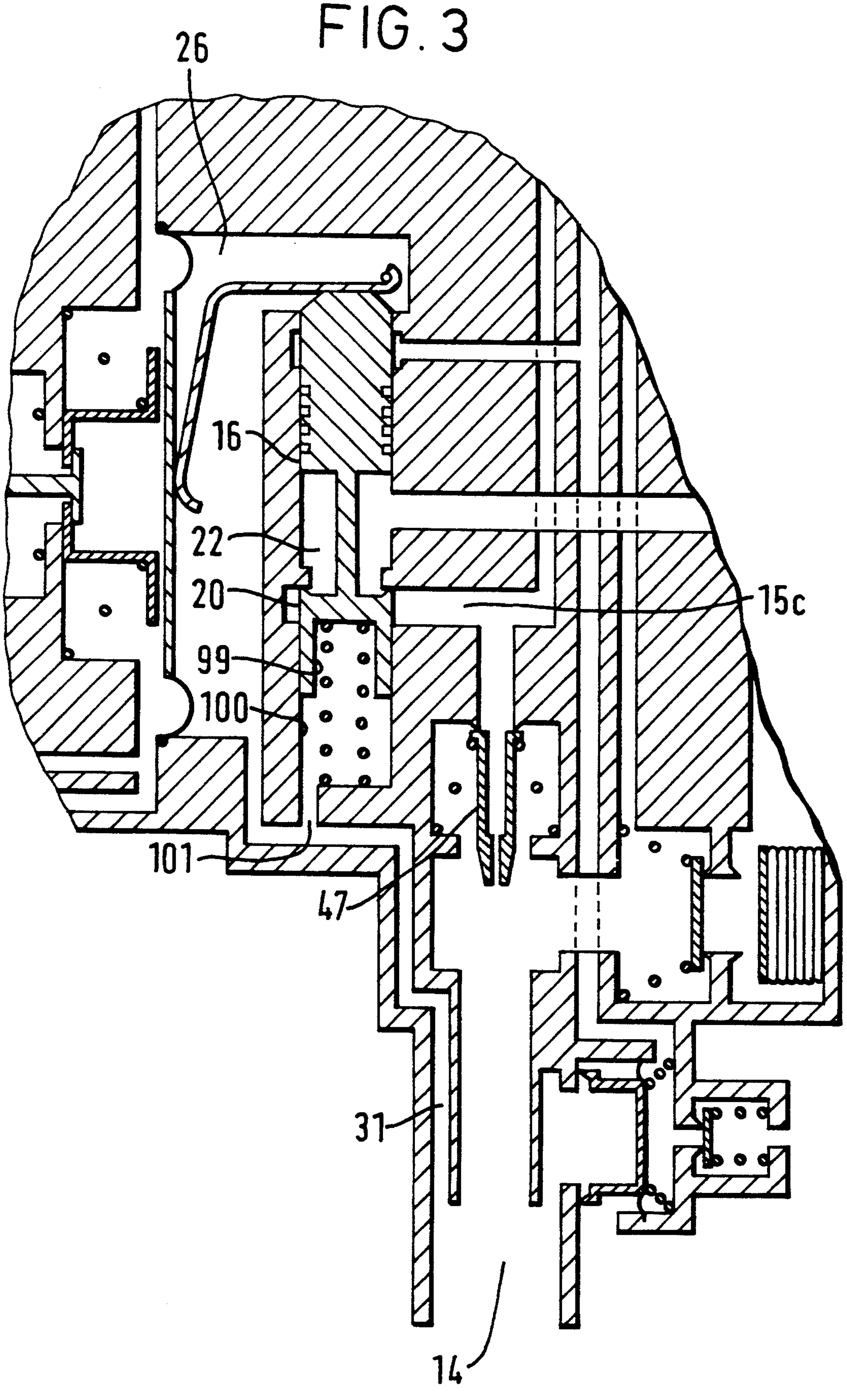
FIG. 3 is a schematic illustration of a part of a breathing demand regulator in accordance with a further embodiment of the invention.

A regulator in accordance with another embodiment of the invention provides demand valve pressure balancing means which nullifies the action of pressure downstream of the demand valve head by inhibiting feedback of downstream pressure onto the demand valve head. In this embodiment, as illustrated in FIG. 3, the demand valve 16 has a demand valve head 20 formed as a hollow piston 99 which slides in a bore 100. In this embodiment passageway 15*c* connects inlet chamber 22 with injector nozzle 47 and is closed by the piston 99 when the demand valve head is in the closed position, as seen in FIG. 3, so that pressure downstream of the demand valve is inhibited from access to the back face of the piston 99. The bore 100, and hence the back face of the piston, is communicated by a passageway 101 with passageway 31 which connects demand pressure sensing chamber 26 with breathing gas outlet 14 so that at its extreme end faces the demand valve 16 is balanced with respect to pressure in chamber 26.

Of course, the invention should not be considered to be limited to the regulator embodiments hereinbefore described with reference to and as shown in the accompanying drawings. For example, the invention may be embodied in a regulator which does not include provision for controlling inflation of a G-suit. Also, a regulator embodying the invention may be used with oxygen-enriched breathing gas supplied by an OBOGS or with 100% oxygen gas supplied by a LOX system or other source of oxygen gas such as a pressurised gas cylinder.

What is claimed is:

1. An aircrew breathing demand regulator (1) for controlling delivery of breathing gas in accordance with breathing demands of an end user, comprising a regulator body (11); a first inlet (12) for receiving a flow of oxygen-enriched breathing gas; an outlet (14) for delivering breathing gas to the end user; a passageway (15) communicating the first inlet with the outlet; a demand valve (16) connected in the passageway between the first inlet and the outlet, the demand valve (16) including a valve head (20) for controlling flow of oxygen-enriched breathing gas from the first inlet to the outlet; breathing demand sensing means (26, 27, 28) connected with the demand valve (16) and operable in response to sensed breathing demand at the outlet (14) for moving the demand valve (16) towards opening; a second inlet (13) communicating the passageway downstream of the demand valve (16) with ambient atmosphere; an ambient air control valve (49, 50) for closing communication between the passageway and the second inlet (13); ambient air entrainment means (47) connected in the passageway for opening the ambient air control valve (49, 50) and entraining ambient air to enter the second inlet (13) and flow to the passageway; and balancing means (64, 95, 99) connected with the demand valve for nullifying feedback of pressure downstream of the demand valve onto the demand valve head.

2. A regulator according to claim 1, wherein the said balancing means (99) comprises means (100, 101) for applying pressure downstream of the demand valve (16) as a balancing force acting on the demand valve in a direction opposing the action of downstream pressure tending to force the demand valve closed.

3. A regulator according to claim 2, wherein said balancing means for applying pressure to downstream of the demand valve as a balancing force comprises a balancing member (99) of equal area to a valve head (20) of the demand valve (16) and means (100, 101) for applying downstream pressure to the balancing member whereby a force is applied to the demand valve oppose the action of downstream pressure tending to force the demand valve closed.

4. A regulator according to claim 3, wherein the demand valve head (20) is formed as a piston (99) sliding in a bore (100) in the regulator body, and vent means (101) are provided in the regulator body for venting the bore to a demand pressure sensing chamber (26) of the regulator.

5. A regulator as claimed in claim 1, wherein the demand valve comprises a valve head (20) supported by a spindle (19) from a spool (17) slideably located in a bore in the regulator body, the valve head and the spool having opposed faces of equal area exposed to pressure of oxygen-enriched breathing gas entering the oxygen-enriched breathing gas inlet whereby the demand valve is balanced with respect to upstream pressure.

6. A regulator as claimed in claim 1, wherein the breathing demand sensing means comprises a demand pressure sensing chamber (26) having connection with the regulator outlet (14), a demand pressure control chamber (29), a diaphragm (28) supported by the regulator body so as to separate the demand pressure sensing chamber from the demand pressure control chamber, and a pivoted operating lever (25) located in the demand pressure sensing chamber so as to contact the diaphragm and the demand valve whereby the demand valve is moved towards opening when breathing demand is sensed in the demand pressure sensing chamber.

7. A regulator according to claim 1 in combination with G-suit inflation control valve means provided integrally with the regulator body for controlling supply of high pressure air to inflate a trouser garment.

* * * * *